United States Patent [19]
Knoll et al.

[11] Patent Number: 5,242,398
[45] Date of Patent: Sep. 7, 1993

[54] CATHETER ASSEMBLY AND RELATED METHOD

[76] Inventors: Charles L. Knoll, 52 Crescent Ave., Passaic, N.J. 07055; Eugene Wexler, 133 Lexington Ave., New York, N.Y. 10016; Peter J. Wilk, 185 West End Ave., New York, N.Y. 10023

[21] Appl. No.: 850,433

[22] Filed: Mar. 12, 1992

[51] Int. Cl.⁵ .............................................. A61M 29/00
[52] U.S. Cl. ..................................... 604/101; 604/171; 604/49; 604/54
[58] Field of Search ............... 604/101, 96, 171, 163, 604/275, 278, 250, 54, 49

[56] References Cited

U.S. PATENT DOCUMENTS

| | | | |
|---|---|---|---|
| 1,120,549 | 12/1914 | Schellberg | 604/171 |
| 2,936,760 | 5/1960 | Gants | 604/101 |
| 4,062,363 | 12/1977 | Bonner, Jr. | 604/171 |
| 4,327,735 | 5/1982 | Hampson . | |
| 4,327,736 | 5/1982 | Inoue | 604/101 |
| 4,710,169 | 12/1987 | Christopher | 604/171 X |

*Primary Examiner*—John D. Yasko
*Attorney, Agent, or Firm*—R. Neil Sudol; Henry D. Coleman

[57] ABSTRACT

A catheter assembly comprises a catheter and a sheath enclosing the catheter to preserve the sterility thereof, the sheath being provided with a plurality of fold lines which form accordion-like pleats to enable a collapse of the sheath at a point of insertion of the catheter into a patient. The sheath is provided at a distal end of the catheter with a flange for engaging a patient during an insertion of the catheter into the patient. A catheter assembly also comprises an anchor balloon attached to the catheter at a distal end thereof, an ancillary balloon attached to the catheter at a point spaced in a proximal direction from the anchor balloon, a tube connecting the ancillary balloon to the anchor balloon so as to enable communication therebetween, and a flow stop mounted to the catheter for preventing fluid from returning to the tube from the anchor balloon upon a pressurization of the anchor balloon with fluid forced from the tube by an application of pressure to the ancillary balloon. A hollow catheter plug defining a flash chamber and having a transparent wall is connected to the catheter at a proximal end thereof for communicating with the catheter. A valve is connected to the plug for preventing fluid flow from the flash chamber.

45 Claims, 6 Drawing Sheets

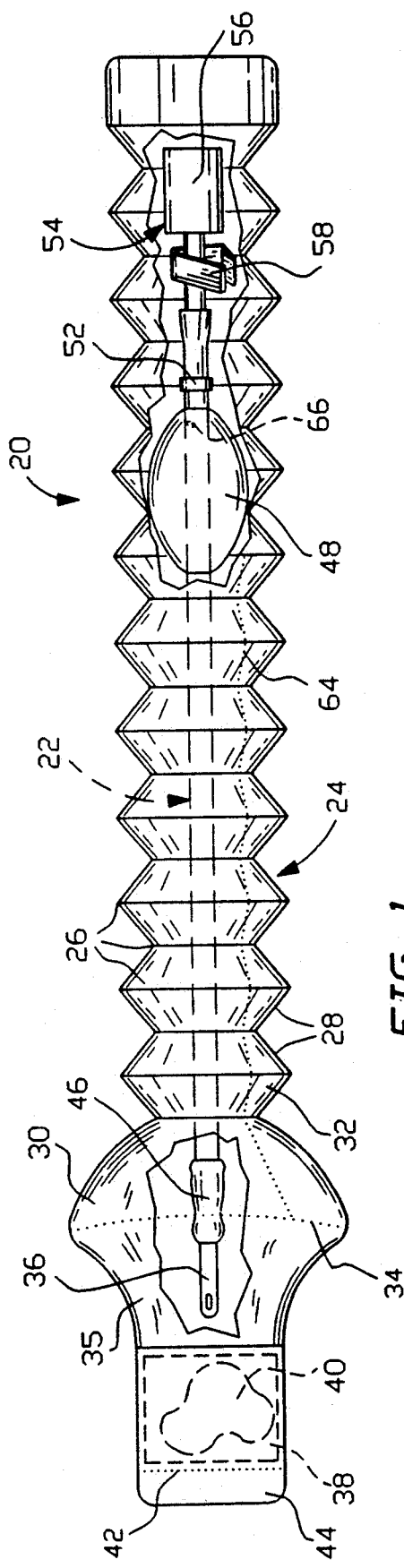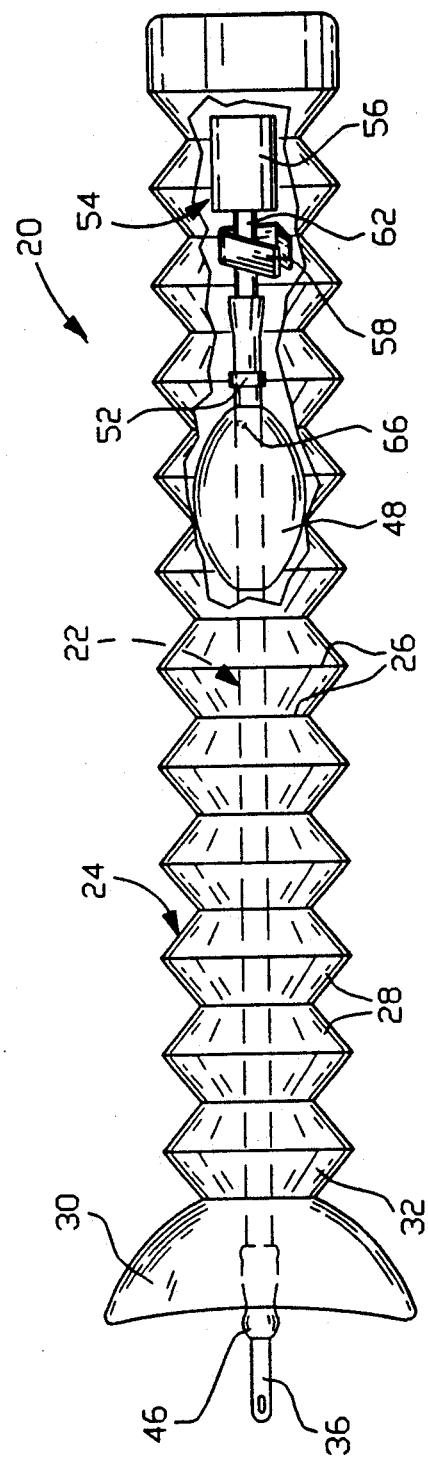

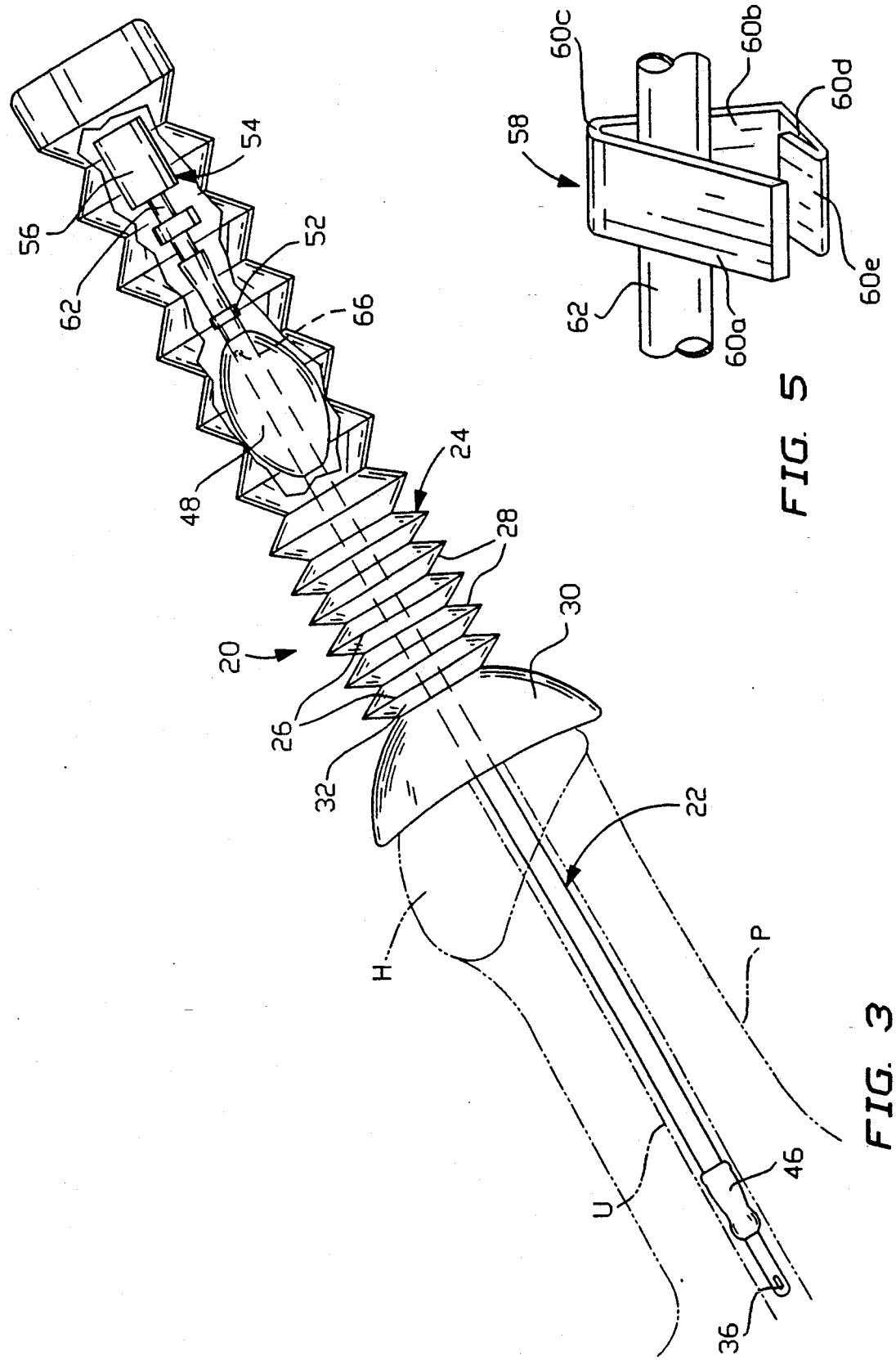

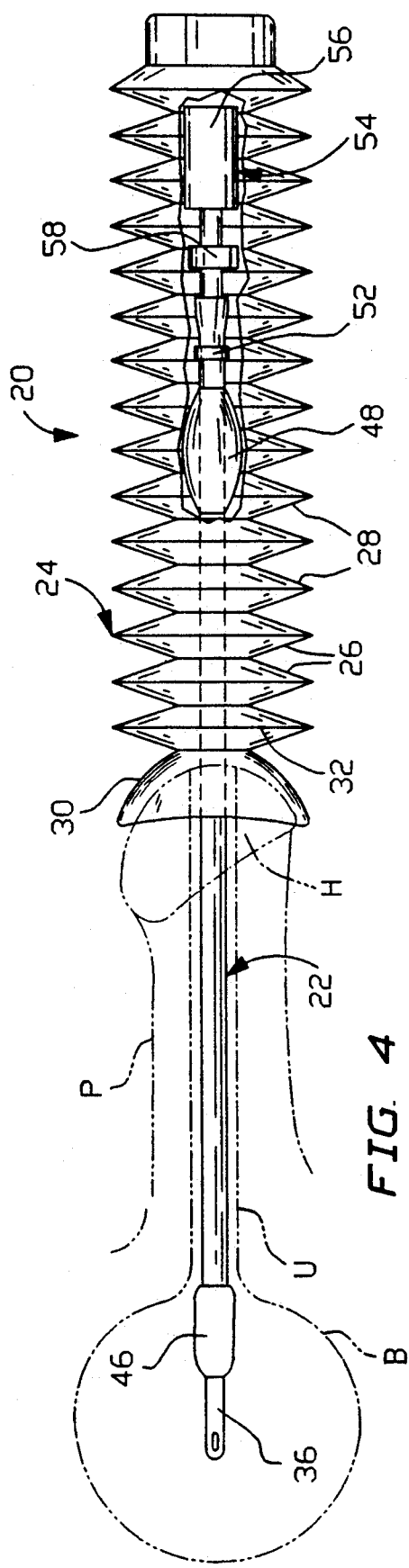
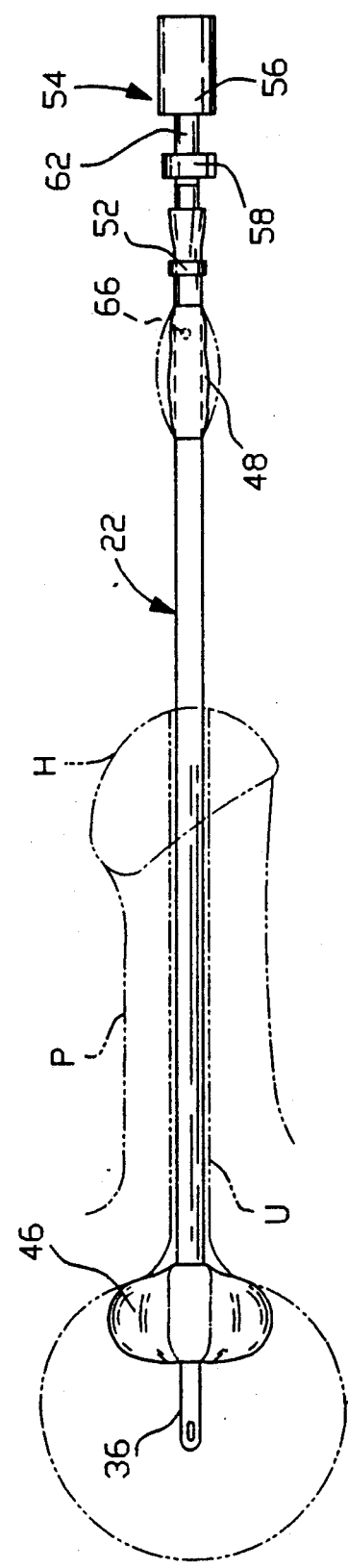
FIG. 4
FIG. 6

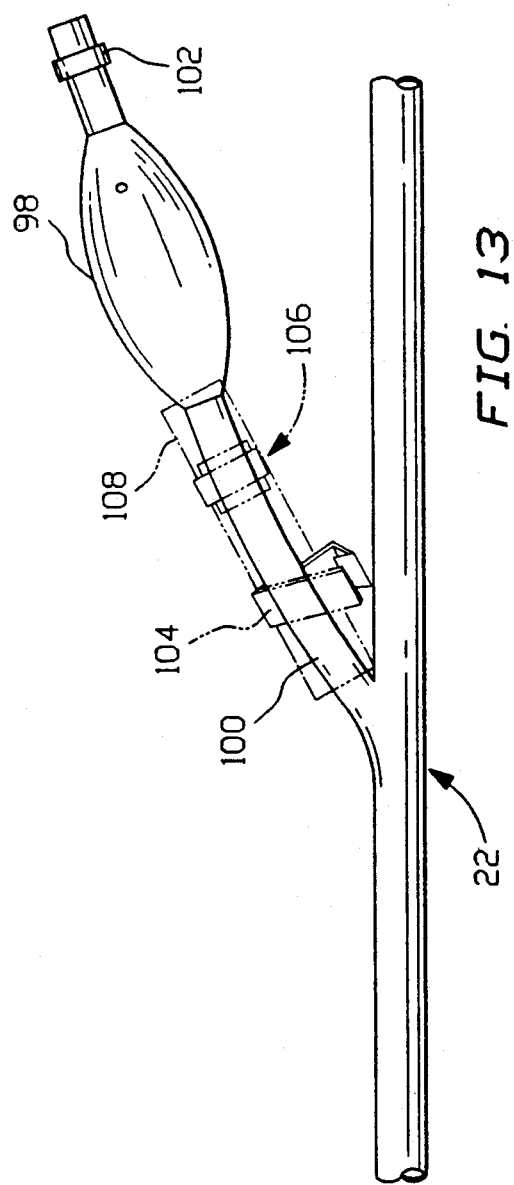
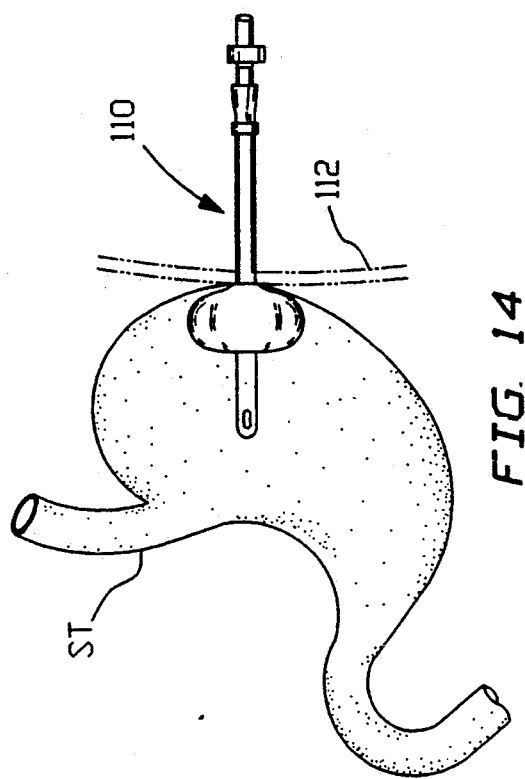
FIG. 13
FIG. 14

CATHETER ASSEMBLY AND RELATED METHOD

BACKGROUND OF THE INVENTION

This invention relates to a catheter assembly. More particularly, this invention relates to a catheter with a sterile sheath and to a catheter with a balloon at a distal end for anchoring the distal end of the catheter in an organ of a patient. This invention also relates to a method for inserting a catheter into a patient and to a method for anchoring the catheter in the patient.

In the medically assisted drainage of bladders, a Foley catheter is inserted through the urethra so that a distal end of the catheter is disposed in the bladder. A balloon attached to the distal end of the catheter is inflated to anchor or hold the catheter in the bladder to permit continued drainage of fluid from the bladder through the catheter. The balloon is inflated via a syringe connected to the balloon via a tube connected to the catheter. In order to determine that the balloon is properly positioned inside the bladder prior to the inflation of the balloon, the proximal end of the catheter is monitored for the flow of urine. The urine generally runs out over the patient and onto protective sheets which have been placed over and under the patient in the crotch area.

Thus, the conventional procedure for inserting a Foley catheter through a patient's urethra and into the bladder is a messy and delicate procedure. Great care must be taken in ensuring that the catheter does not come into contact with any nonsterile objects prior to insertion of the catheter through the urethra. Maintaining the sterility of the catheter is difficult insofar as the catheter is a flexible member and flops about prior to deployment in the patient's urethra. Moreover, although sterile gloves are provided in Foley catheter kits, the physician must frequently handle a number of potentially nonsterile objects immediately prior to inserting the catheter into the patient's urethra.

The difficulty in manipulating the catheter is exacerbated by the ancillary components attached to the catheter, including the syringe with the balloon pressurization fluid, and a urine collection bag.

A Foley catheter always comes enclosed in a sterile sheath or bag. Although some physicians attempt to manipulate the catheter through the sheath, to avoid contamination of the catheter during the insertion procedure, the sheath's construction militates against using the sheath as an insertion tool. The sheath does not collapse about the catheter, as required in such a procedure. Accordingly, the sheath is generally removed from the catheter, or at least from the distal end thereof, prior to an insertion or deployment procedure.

Once an anchoring balloon has been properly inflated via the syringe, the tube connecting the syringe to the anchoring balloon is closed, to prevent deflation of the balloon. The syringe is then removed and discarded. When the catheter is to be removed from the patient, another syringe must be connected to the catheter to draw the pressurization fluid from the anchoring balloon to deflate the balloon.

Catheters with anchoring balloons are used for other purposes, as well as to drain the bladder. For example, catheters are inserted into the stomach of some patients through incisions in the skin tissues to facilitate feeding of such patients. Endotracheal tubes are also used in some circumstances.

OBJECTS OF THE INVENTION

An object of the present invention is to provide a catheter assembly of the above-described type wherein the insertion procedure is facilitated.

Another object of the present invention is to provide such a catheter assembly wherein the maintenance of sterility during the insertion or deployment of the catheter is enhanced.

Another, more particular, object of the present invention is to provide such a catheter assembly which has fewer separate parts than conventional catheter assemblies and which, accordingly, is easier to use.

A further particular object of the present invention is to provide such a catheter assembly which requires less storage space.

Yet another particular object of the present invention is to provide such a catheter assembly which has fewer discarded pieces.

An additional object of the present invention is to provide an improved method for inserting a catheter into an organ of a patient and anchoring the catheter in the organ.

Another, more particular, object of the present invention is to provide such a method wherein the maintenance of sterility is facilitated.

A further particular object of the present invention is to provide such a method which entails less spillage of body fluids.

SUMMARY OF THE INVENTION

A catheter assembly comprises, in accordance with the present invention, a catheter and a sheath enclosing the catheter to preserve the sterility thereof, the sheath being provided with a plurality of fold lines to enable a collapse of the sheath at a point of insertion of the catheter into a patient.

According to another feature of the present invention, the sheath is provided at a distal end of the catheter with a flange for engaging a patient during an insertion of the catheter into the patient. The flange is preferably cup-shaped in the event that the catheter is a Foley-type catheter. In addition, the flange is preferably substantially rigid, i.e., not flexible like a film or sheet, to enable a physician to hold the distal end of the catheter at an insertion point on the patient.

According to a further feature of the present invention, the sheath is provided with a score line at a distal end, distally of the flange, to enable a tearing off of a distal end portion of the sheath to expose a tip of the catheter. Moreover, the sheath may include a body portion containing the catheter and, at a distal end of the body portion, a chamber separable from the body portion, an aliquot of an antibacterial agent being disposed in the chamber. A piece of cotton or other swab may be disposed in the chamber and soaked with the antibacterial agent (e.g., betadine). The sheath is advantageously provided with a score line distally of the chamber to enable a tearing off of a terminal portion of the sheath to expose the antibacterial agent to enable an application thereof to an insertion site on a patient.

Pursuant to a particular feature of the present invention, the fold lines are circular and define a plurality of collapsible pleats in the sheath.

A catheter assembly in accordance with a specific embodiment of the present invention also includes an anchor balloon attached to the catheter at a distal end thereof, an ancillary balloon attached to the catheter at a point spaced in a proximal direction from the anchor balloon, a tube connecting the ancillary balloon to the anchor balloon so as to enable communication therebetween, and a flow stop mounted to the catheter for preventing fluid from returning to the tube from the anchor balloon upon a pressurization of the anchor balloon with fluid forced from the tube by an application of pressure to the ancillary balloon.

In this embodiment of the invention, the anchor balloon, the tube and the ancillary balloon contain the fluid in a closed system. The anchor balloon is a high pressure balloon, whereas the ancillary balloon is a low pressure balloon. More specifically, the anchor balloon is defined by a first wall and the ancillary balloon is defined by a second wall, the first wall being less stretchable than the second wall. Thus, a pressurizing fluid in the anchor balloon, the ancillary balloon and the tube is at a higher pressure when the anchor balloon and the ancillary balloon are in an expanded state and a collapsed state, respectively, than when the anchor balloon and the ancillary balloon are in a collapsed state and an expanded state, respectively.

Pursuant to an even more particular feature of the present invention, the ancillary balloon surrounds the catheter and the tube. Alternatively, the ancillary balloon is connected to the catheter via the tube.

The flow stop may take the form of a locking mechanism operatively connected to the tube for blocking communication between the anchor balloon and the ancillary balloon. More particularly, the locking mechanism includes a clamp such as a clip or an elastic band for closing off the tube. Alternatively, the locking mechanism includes a valve having an opened position and a closed position.

As yet another particular alternative, the flow stop includes a substantially rigid sleeve movably attached to the catheter for sliding over the ancillary balloon and thereby preventing a reinflation thereof with fluid from the anchor balloon.

According to yet another feature of the present invention, a hollow catheter plug defining a flash chamber and having a transparent wall is connected to the catheter at a proximal end thereof for communicating with the catheter. A valve is connected to the plug for preventing fluid flow from the flash chamber.

The valve may specifically take the form of a clamp such as a clip for closing off a tube connecting the flash chamber to the catheter. Alternatively, the valve includes a tube inside the chamber, defining therewith a type of labyrinthine seal.

A method for inserting a catheter into a body organ of a patient comprises, in accordance with the present invention, the steps of (a) providing a catheter enclosed by an internally sterile sheath, (b) removing a distal end portion of the sheath so as to expose a distal end only of the catheter, (c) inserting the distal end of the catheter into a patient, and (d) manipulating the catheter through the sheath to push the catheter into the patient while simultaneously collapsing the sheath into a shortened accordion-like configuration at a point of insertion of the catheter into the patient.

Pursuant to another feature of the present invention, the catheter insertion procedure further comprises the step of engaging the patient about the point of insertion with a flange provided at a distal end of the sheath. Where the sheath is provided with a score line distally of the flange, the step of removing a distal end portion of the sheath includes the step of tearing off the distal end portion of the sheath at the score line.

Where the sheath has a body portion containing the catheter and, at a distal end of the body portion, a chamber separable from the body portion, an aliquot of an antibacterial agent being disposed in the chamber, the catheter insertion procedure further comprises the steps of tearing off a tip of the sheath to expose the antibacterial agent and applying the antibacterial agent to the patient about the point of insertion prior to the step of removing a distal end portion of the sheath.

A method for inserting a catheter into a body organ of a patient comprises, in accordance with the present invention, additional steps of (i) inserting a catheter into a patient, the catheter having an anchor balloon at a distal end, (ii) applying pressure to an ancillary balloon at a proximal end of the catheter to squeeze a pressurizing fluid from the ancillary balloon towards the anchor balloon, and (iii) upon an expansion of the anchor balloon in response to the application of pressure to the ancillary balloon, preventing fluid from flowing back from the anchor balloon towards the ancillary balloon.

Pursuant to another feature of the present invention, the step of preventing fluid flowback includes the step of closing communication between the anchor balloon and the ancillary balloon. The closing of communication may be effectuated by clamping a tube extending between the anchor balloon and the ancillary balloon. Alternatively, the closing of communication may be effectuated by actuating a valve to block communication between the anchor balloon and the ancillary balloon. Preventing fluid flowback may alternatively or additionally include the step of sliding a sleeve over the ancillary balloon to prevent a reinflation thereof with fluid.

Where the catheter is provided at a proximal end with a hollow catheter plug defining a flash chamber having a transparent wall, the catheter insertion or deployment procedure further comprises the step of actuating a valve connected to the plug for preventing fluid flow from the chamber.

A catheter assembly in accordance with the present invention enhances sterility insofar as the catheter leaves the sterile containment sheath only at the point of insertion into the patient. The catheter thus remains continually protected by the sheath even during the insertion procedure. The sheath surrounds both the catheter and a region of the patient's body about the point of insertion of the catheter.

A catheter assembly in accordance with the present invention has fewer separate parts than conventional catheter assemblies. The pressurization syringe is eliminated. Moreover, no additional syringe is required to depressurize the anchor balloon prior to removal thereof.

A catherization assembly in accordance with the present invention has fewer discarded parts and therefore reduces medical waste. No syringes are needed to implement a catheterization method in accordance with the present invention.

A catheter assembly in accordance with the present invention requires less storage space than the conventional catheterization kit. No special sterile gloves are needed. The ancillary balloon takes up less space than a pressurization syringe. The antibacterial agent (e.g., betadine) does not requires a separate container, but is instead housed in the catheter sheath.

For each of the foregoing reasons, a catheterization method using a catheter assembly in accordance with the present invention constitutes an improved method for inserting a catheter into an organ of a patient and anchoring the catheter in the organ. The maintenance of sterility is facilitated. In addition, the procedure entails less mess than the conventional technique. There is, for example, less spillage of body fluids than in the conventional technique.

BRIEF DESCRIPTION OF THE DRAWING

FIG. 1 is a side elevational view, partly broken away, of a catheter assembly in accordance with the present invention.

FIG. 2 is a side elevational view, partly broken away, of the catheter assembly of FIG. 1, showing a distal end portion of a sheath member removed.

FIG. 3 is a side elevational view, partly broken away, of the catheter assembly of FIGS. 1 and 2, showing a catheter partly inserted into a patient's urethra and the sheath member in a partly collapsed configuration.

FIG. 4 is a side elevational view, partly broken away, similar to FIG. 3, showing the distal end of the catheter protruding into the patient's bladder and the sheath member in a substantially collapsed configuration.

FIG. 5 is a perspective view of a clip included in the catheter assembly of FIGS. 1-4.

FIG. 6 is a side elevational view of the catheter of FIGS. 1-4, with the sheath member removed and an anchor balloon inflated at the distal end of the catheter.

FIG. 13 is a partial side elevational view, partly in cross-section, showing several additional alternative modifications of the catheter assembly of FIGS. 1-4 and 6.

FIG. 14 is a schematic view showing use of a catheter assembly in accordance with the present invention for use in supplying nutritive fluids to a person's stomach.

DETAILED DESCRIPTION

Figure 7:
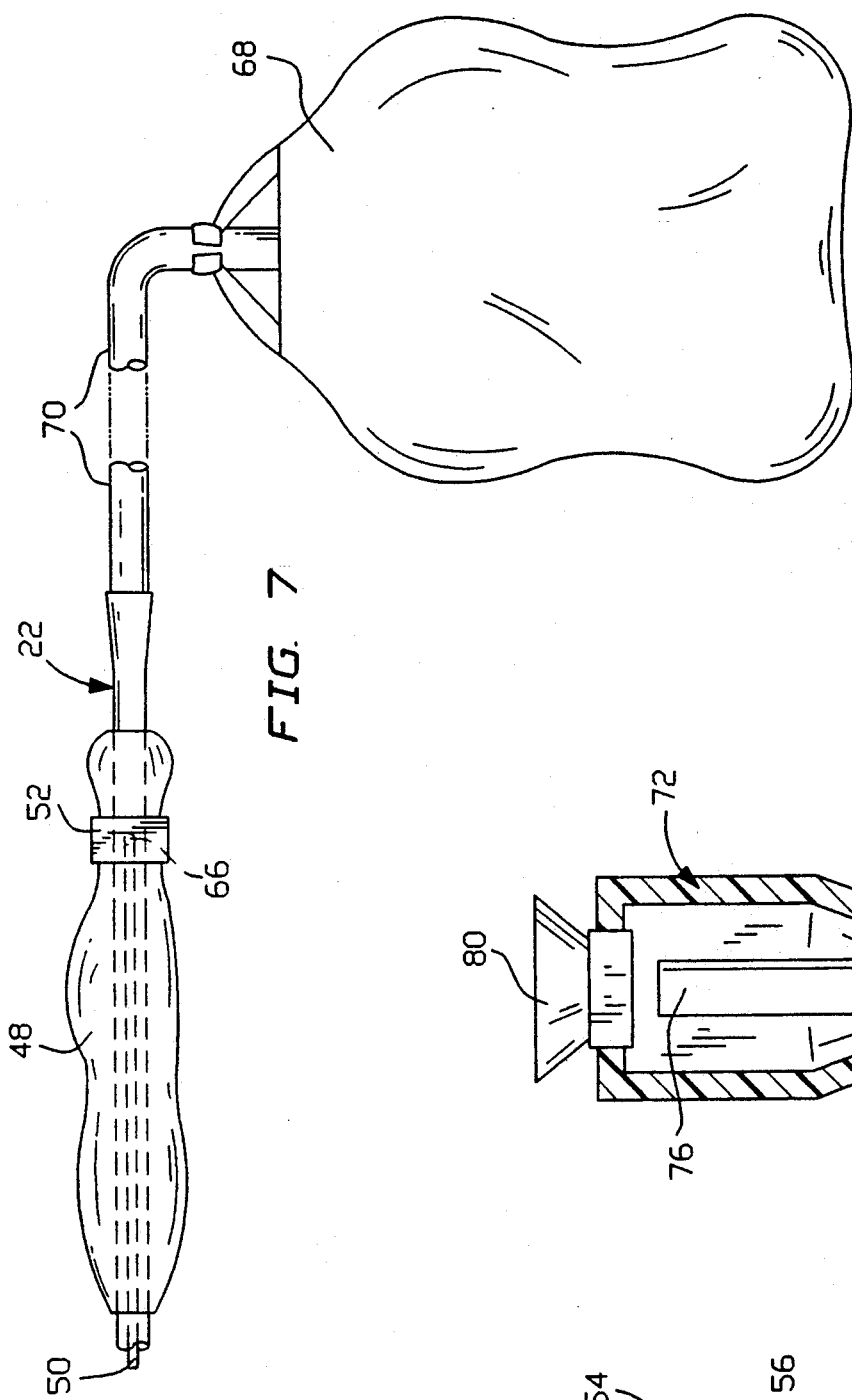
FIG. 7 is a partial side elevational view of the catheter of FIGS. 1-5, showing attachment of a proximal end of the catheter to a urine collection bag.

As illustrated in FIG. 1, a catheter assembly 20 comprises a catheter 22 and a sheath 24 enclosing the catheter to preserve the sterility thereof. Sheath 24 is provided with a plurality of circular fold lines 26 to form a plurality of annular pleats 28. Fold lines 26 enable a collapse of sheath 24 into a shortened accordion-like configuration (FIGS. 3 and 4) at a point of insertion of catheter 22 into a patient. Sheath 24 may be made of a flexible polymeric material such as polyethylene which has a sufficient rigidity or thickness to facilitate the collapsing of the sheath during an insertion or catheterization procedure.

Sheath 24 is provided at a distal end of catheter 22 with a flange 30 for engaging a patient during an insertion of the catheter into the patient. Flange 30 is preferably cup-shaped where catheter 22 is a Foley-type catheter, for use in draining a man's bladder. In addition, flange 30 has a greater rigidity than a body portion 32 of sheath 24. Flange 30 is not flexible like a film or sheet and enables a physician to hold the distal end of catheter 22 at an insertion point on the patient, as shown in FIGS. 3 and 4.

Sheath 24 is provided with a score line 34 at a distal end, distally of flange 30, to enable a tearing off of a distal end portion 35 of the sheath to expose a tip 36 of catheter 22, as illustrated in FIG. 2. At a distal end of body portion 32 of catheter 22 is disposed a chamber 38 separable from body portion 32 and containing a cotton swab 40 soaked with an aliquot of an antibacterial agent such a betadine. Sheath 24 is further provided with another score line 42 distally of chamber 38 to enable a tearing off of a terminal portion 44 of sheath 24 to expose swab 40 to enable an application of the antibacterial agent to an insertion site on a patient prior to an insertion of catheter tip 36. It is to be noted that, the antibacterial agent may be provided by itself in chamber 38, that is, without swab 40. In that case, the antibacterial agent may be dispersed in a lubricating gel (not shown) which may be used to anoint catheter tip 36 prior to an insertion thereof into the patient. Alternatively, an auxiliary chamber (not shown) may be provided at the distal end of sheath 24 for storing an aliquot of a lubricating medium.

As illustrated in FIGS. 1-4 and 6, catheter assembly 20 also comprises an anchor balloon 46 attached to catheter 22 at a distal end thereof. As shown in FIG. 1, anchor balloon 46 is initially in a deflated configuration. An ancillary balloon 48 containing a reservoir of a pressurization fluid is attached to catheter 22 at proximal end of the catheter. Ancillary balloon 48, like anchor balloon 46, surrounds catheter 22. A tube 50 (FIG. 7) connects ancillary balloon 48 to anchor balloon 46 so as to enable communication therebetween.

Anchor balloon 46, ancillary balloon 48 and tube 50 contain pressurization fluid in a closed system. Anchor balloon 46 has a wall which is tighter or less stretchable that the wall defining ancillary balloon 48. Accordingly, anchor balloon 46 is a high pressure balloon, whereas ancillary balloon 48 is a low pressure balloon. Without the application of external pressure to the system, anchor balloon 46 is deflated while ancillary balloon 48 is inflated, as illustrated in FIGS. 1-4. The application of external pressure to ancillary balloon 48, e.g., by squeezing that balloon with one's hand, causes pressurization fluid to flow from ancillary balloon 48 into tube 50 and from tube 50 into anchor balloon 46, thereby inflating the anchor balloon.

Catheter assembly 20 further comprises a flow stop in the form of a rubber band or other elastic clamp 52 mounted to catheter 22 for enabling a physician or other appropriate user to block the flow of pressurization fluid back into ancillary balloon 48 and thereby maintain anchor balloon 46 in an inflated configuration. The arresting of fluid flow prevents pressurization fluid from returning to tube 50 from anchor balloon 46 upon a pressurization of the anchor balloon with fluid forced from the tube by an application of pressure to ancillary balloon 48.

A hollow catheter plug 54 is attached to the proximal end of catheter 22 and includes a flash chamber receptacle 56 which has a transparent wall. A valve 58 in the form of a spring clip is connected to plug 54 for preventing fluid flow from flash chamber receptacle 56.

In using the catheter assembly 20 of FIG. 1, a physician or assistant rips off terminal portion 44 via score line 42, thereby exposing swab 40 and the antibacterial agent carried thereby. Swab 40 is manipulated via the distal end portion of sheath 24 to sterilize a region of the patient about the point of insertion of catheter 22.

As discussed above, a lubricant carried at the distal end of sheath 24 may be used to anoint catheter tip 36 to facilitate insertion of catheter 22 into a patient.

Upon the completion of the preparation, distal end portion 35 of sheath 24 is removed from sheath body 32 along score line 34 (compare FIGS. 1 and 2). Flange 30 is then brought into engagement with the patient about a point of insertion of catheter 22. As illustrated in FIG. 3, flange 30 is placed to cup the head H of a patient's penis P. Distal tip 36 of catheter 22 is then inserted into the urethra U of the patient, as further illustrated in FIG. 3. In implementing the insertion of catheter 22, the physician manipulates catheter 22 through sheath 24 to push the catheter into urethra U while simultaneously collapsing the sheath into a shortened accordion-like configuration at penis head H.

Upon the appearance of urine inside flash chamber receptacle 56, indicating that distal tip 36 has penetrated to the patient's bladder B, as depicted in FIG. 4, clip valve member 58 is actuated to close off communication between flash chamber receptacle 56 and catheter 22. Clip valve member 58 is shown in detail in FIG. 5 and may comprise a pair of leg members 60a and 60b connected to one another at a bight 60c and including a base 60d with a detent 60e for engaging a tip of leg 60a to close the clip about a tube 62 of catheter plug 54.

Also upon the appearance of urine inside flash chamber receptacle 56, sheath 24 is removed from the proximal end of catheter 22, for example, by tearing along a longitudinal score line 64 (FIG. 1). Manual pressure is then applied to ancillary balloon 48 to squeeze pressurization fluid therefrom into tube 50 (FIG. 7) and along tube 50 into anchor balloon 46 to inflate the anchor balloon, as illustrated in FIG. 6. Rubber band 52 is then moved from its storage position shown in FIGS. 1-4 to a clamping position shown in FIG. 7. The clamping position may be over an opening 66 through which fluid passes between tube 50 and ancillary balloon 48. Alternatively, the clamping position may be located distally of opening 66, whereby tube 50 is squeezed shut to block communication between anchor balloon 46 and ancillary balloon 48. In the clamping position, rubber band 52 prevents fluid flow along tube 50 and particularly from anchor balloon 46. Of course, the clamping of tube 50 does not close the catheter. To that end catheter 22 may be made of a more rigid material, particularly in the region of ancillary balloon 48.

Figure 8:
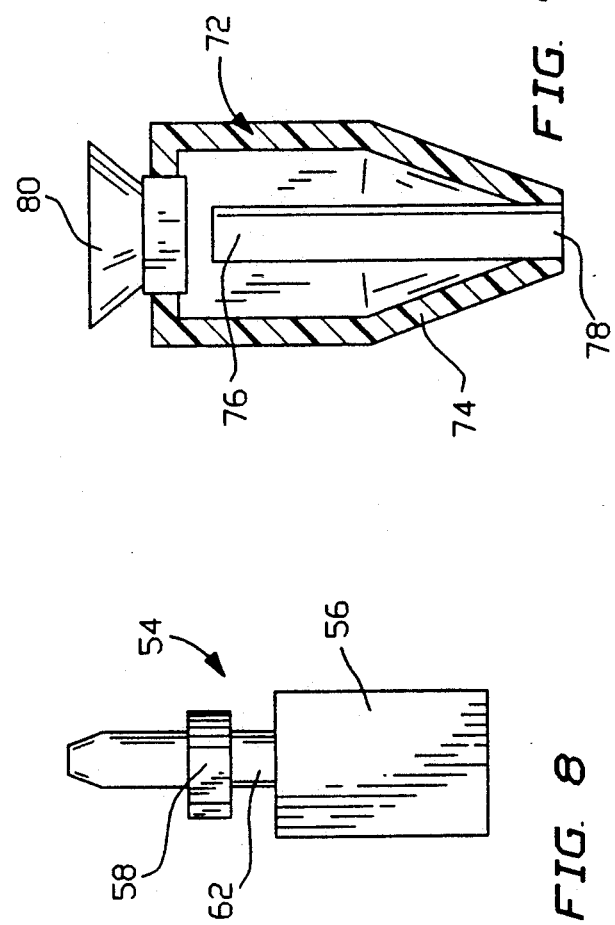
FIG. 8 is a side elevational view of a flash chamber member included in the catheter assembly of FIGS. 1-4 and 6, the flash chamber member being removed from the catheter assembly.

As further depicted in FIG. 7, flash chamber receptacle 56 is removed from catheter 22 at the end of the catheterization procedure and a collection bag 68 is connected to catheter 22 via a tube 70. Flash chamber receptacle 56 is shown separately in FIG. 8. It contains a urine specimen and may be transported to a laboratory for analysis of the specimen.

Figure 9:
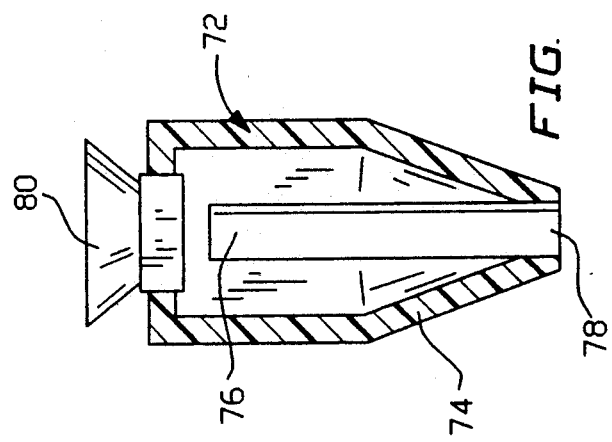
FIG. 9 is a longitudinal cross-sectional view of another flash chamber member in accordance with the present invention.

An alternative flash chamber design is illustrated in FIG. 9. A chamber body 72 has a tapered end 74 for insertion into the proximal end of catheter 22. A tube 76 extends from an opening 78 on tapered end 74 partially through chamber body 72, thereby defining therewith a type of labyrinthine seal or valve. A removable cap 80 on chamber body 72 enables access to a urine specimen for testing purposes.

Figure 10:
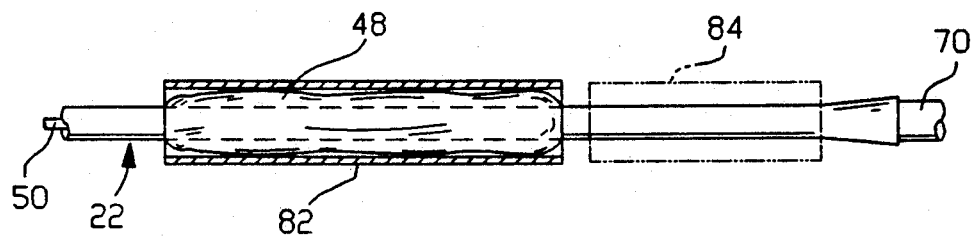
FIG. 10 is a partial side elevational view, partly in cross-section, of a modification of the catheter assembly of FIGS. 1-4 and 6.

As illustrated in FIG. 10, the flow stop for the balloon pressurization fluid may take the form of a substantially rigid sleeve 82 movably attached to catheter 22 for sliding over ancillary balloon 48 and thereby preventing a reinflation thereof with fluid from anchor balloon 46. Prior to actuation of this sleeve valve, sleeve 82 is in a storage position juxtaposed to ancillary balloon 48, as indicated in phantom lines at 84.

Figure 11:
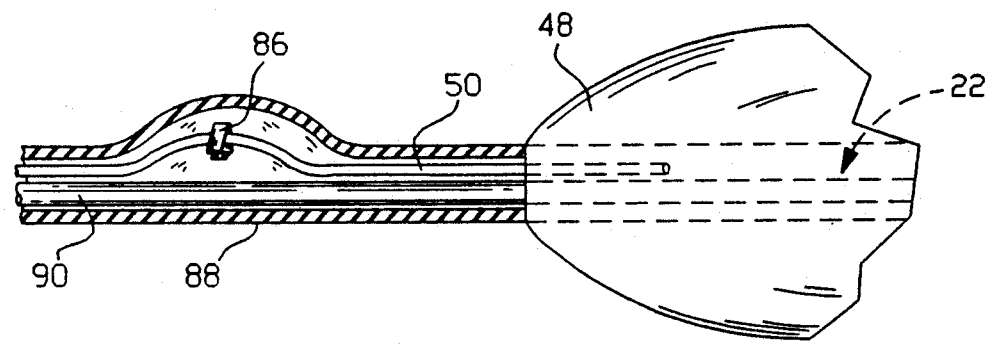
FIG. 11 is a partial side elevational view, partly in cross-section, of an alternative modification of the catheter assembly of FIGS. 1-4 and 6.

As another alternative to the flow stop for the balloon pressurization fluid, FIG. 11 shows a toggle-type clip 86 disposed inside a tubular casing 88 of catheter 22. Clip 86 surrounds tube 50 and enables a releasable clamping thereof by manipulation of the clip through the material of casing 88. Catheter 22 includes a catheter duct 90 extending through casing 88 separately from tube 50.

Figure 12:
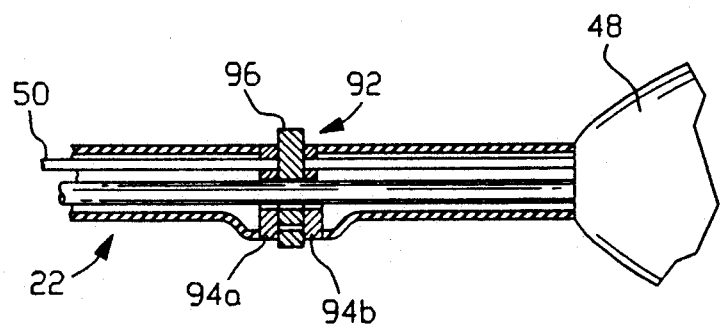
FIG. 12 is a partial side elevational view, partly in cross-section, of another modification of the catheter assembly of FIGS. 1-4 and 6.

In another modification of the catheter assembly 20, the flow stop for the balloon pressurization fluid comprises a valve 92 illustrated in FIG. 12. Valve 92 includes a pair of annular holders 94a and 94b connected to casing 88 and a rotary valve member 96 sandwiched between holders 94a and 94b.

FIG. 13 depicts a modified embodiment of catheter assembly 20 wherein an ancillary balloon 98 is connected to catheter 22 via a pressurization fluid tube 100. As discussed hereinabove, a flow stop for balloon pressurization fluid may take the form of a rubber band or elastic clamp 102, a clip 104, a valve 106 or a sleeve 108.

FIG. 14 shows use of a catheter assembly 110 inserted through a skin surface 112 into a person's stomach ST. Catheter assembly may take any form described herein. A catheter assembly in accordance with the present invention may also be used in endotracheal and other applications.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are profferred by way of example to facilitate comprehension of the invention and should not be construed to limit the scope thereof.

What is claimed is:

1. A catheter assembly comprising:
   a catheter;
   an anchor balloon attached to said catheter at a distal end thereof;
   an ancillary balloon attached to said catheter at a point spaced in a proximal direction from said anchor balloon;
   a tube connecting said ancillary balloon to said anchor balloon so as to enable communication therebetween, said anchor balloon, said tube and said ancillary balloon containing fluid in an essentially closed system to enable expansion of said anchor balloon by at least a partial collapse of said ancillary balloon; and
   flow stoppage means mounted to said catheter for preventing said fluid from returning to said tube from said anchor balloon upon a pressurization of said anchor balloon with fluid forced from said tube by an application of pressure to said ancillary balloon.

2. The catheter assembly defined in claim 1 wherein said flow stoppage means includes locking means operatively connected to said tube for blocking communication between said anchor balloon and said ancillary balloon.

3. The catheter assembly defined in claim 2 wherein said locking means includes clamping means for closing off said tube.

4. The catheter assembly defined in claim 3 wherein said clamping means includes a clip.

5. The catheter assembly defined in claim 3 wherein said clamping means includes an elastic band.

6. The catheter assembly defined in claim 2 wherein said locking means includes a valve having an opened position and a closed position.

7. The catheter assembly defined in claim 1 wherein said flow stoppage means includes a substantially rigid sleeve movably attached to said catheter for sliding over said ancillary balloon and thereby preventing a reinflation thereof with fluid from said anchor balloon.

8. The catheter assembly defined in claim 1 wherein said anchor balloon is defined by a first wall and said ancillary balloon is defined by a second wall, said first wall being less stretchable than said second wall, whereby a pressurizing fluid in said anchor balloon, said ancillary balloon and said tube is at a higher pressure when said anchor balloon and said ancillary balloon are in an expanded state and a collapsed state, respectively, than when said anchor balloon and said ancillary balloon are in a collapsed state and an expanded state, respectively.

9. The catheter assembly defined in claim 1 wherein said ancillary balloon is connected to said catheter via said tube.

10. The catheter assembly defined in claim 1, further comprising:
a hollow catheter plug defining a flash chamber having a transparent wall, said plug being connected to said catheter at a proximal end thereof for communicating with said catheter; and
valve means connected to said plug for preventing fluid flow from said chamber.

11. The catheter assembly defined in claim 1, further comprising a sheath enclosing catheter, said anchor balloon, said ancillary balloon and said tube to preserve the sterility thereof, said sheath being provided with a plurality of fold lines to enable a collapse of said sheath at a point of insertion of said catheter into a patient.

12. A catheter assembly comprising:
a catheter;
a hollow catheter plug defining a flash chamber having a transparent wall, said plug being connected to said catheter at a proximal end thereof for communicating with said catheter; and
valve means connected to said plug for preventing fluid flow from said chamber.

13. A catheter assembly comprising:
a catheter; and
a sheath collapsible in a longitudinal direction and enclosing said catheter to preserve the sterility thereof, said sheath being provided at a distal end of said catheter with a flange for engaging a patient during an insertion of said catheter into the patient, said sheath being provided with a score line distally of said flange to enable a tearing off of a distal end portion of said sheath to expose a distal tip of said catheter.

14. The catheter assembly defined in claim 13 wherein said sheath has a body portion containing said catheter, said flange being disposed at a distal end of said body portion, said sheath being provided distally of said flange with a chamber separable from said flange via said score line, an aliquot of an antibacterial agent being disposed in said chamber.

15. The catheter assembly defined in claim 14, further comprising a swab member disposed in said chamber.

16. The catheter assembly defined in claim 14 wherein said sheath is provided with an additional score line distally of said chamber to enable a tearing off of a distal tip of said sheath to expose said antibacterial agent to enable an application thereof to an insertion site on a patient.

17. The catheter assembly defined in claim 13 wherein said flange is cup shaped.

18. The catheter assembly defined in claim 13 wherein said flange is at least partially rigid.

19. The catheter assembly defined in claim 13, further comprising:
an anchor balloon attached to said catheter at a distal end thereof;
an ancillary balloon attached to said catheter at a point spaced in a proximal direction from said anchor balloon;
a tube connecting said ancillary balloon to said anchor balloon so as to enable communication therebetween; and
flow stoppage means mounted to said catheter for preventing fluid from returning to said tube from said anchor balloon upon a pressurization of said anchor balloon with fluid forced from said tube by an application of pressure to said ancillary balloon, said anchor balloon, said ancillary balloon and said tube being enclosed by said sheath.

20. The catheter assembly defined in claim 13, further comprising:
a hollow catheter plug defining a flash chamber having a transparent wall, said plug being connected to said catheter at a proximal end thereof for communicating with said catheter; and
valve means connected to said plug for preventing fluid flow from said chamber.

21. A catheter assembly comprising:
a catheter;
a sheath collapsible in longitudinal direction, said sheath having a body portion containing said catheter and, at a distal end of said body portion, a chamber separable from said body portion; and
an aliquot of an antibacterial agent disposed in said chamber.

22. The catheter assembly defined in claim 21 wherein said sheath is provided at a distal end of said catheter with a flange for engaging a patient during an insertion of said catheter into the patient.

23. The catheter assembly defined in claim 22 wherein said flange is cup-shaped.

24. The catheter assembly defined in claim 22 wherein said flange is substantially rigid.

25. The catheter assembly defined in claim 21, further comprising:
a hollow catheter plug defining a flash chamber having a transparent wall, said plug being connected to said catheter at a proximal end thereof for communicating with said catheter; and valve means connected to said plug for preventing fluid flow from said chamber.

26. The catheter assembly defined in claim 25 further comprising a swab member disposed in said chamber.

27. The catheter assembly defined in claim 21 wherein
is provided with a score line distally of said chamber to enable a tearing off of a distal end portion of said sheath to expose said antibacterial agent to enable an application thereof to an insertion site on a patient.

28. The catheter assembly defined in claim 21 wherein said sheath is provided with a plurality of fold lines to enable a collapse of said sheath at a point of insertion of said catheter into a patient, said fold lines being circular and defining a plurality of collapsible pleats in said sheath.

29. The catheter assembly defined in claim 21, further comprising:
an anchor balloon attached to said catheter at a distal end thereof;
an ancillary balloon attached to said catheter at a point spaced in a proximal direction from said anchor balloon;
a tube connecting said ancillary balloon to said anchor balloon so as to enable communication therebetween; and
flow stoppage means mounted to said catheter for preventing fluid from returning to said tube from said anchor balloon upon a pressurization of said anchor balloon with fluid forced from said tube by an application of pressure to said ancillary balloon, said anchor balloon, said ancillary balloon and said tube being enclosed by said sheath.

30. A method for inserting a catheter into a body organ of a patient, comprising the steps of:
inserting a catheter into a patient, said catheter having an anchor balloon at a distal end and further having an ancillary balloon communicating with said anchor balloon and disposed proximally thereof, said anchor balloon and said ancillary balloon containing fluid in an essentially closed system, whereby collapse of said ancillary balloon results in an expansion of said anchor balloon;
applying pressure to said ancillary balloon to at least partially collapse said ancillary balloon and thereby squeeze a pressurizing fluid from said ancillary balloon towards said anchor balloon; and
upon an expansion of said anchor balloon in response to the application of pressure to said ancillary balloon, preventing fluid from flowing back from said anchor balloon towards said ancillary balloon.

31. The method defined in claim 30 wherein said step of preventing includes the step of closing communication between said anchor balloon and said ancillary balloon.

32. The method defined in claim 31 wherein said step of closing includes the step of clamping a tube extending between said anchor balloon and said ancillary balloon.

33. The method defined in claim 31 wherein said step of closing includes the step of actuating a valve to block communication between said anchor balloon and said ancillary balloon.

34. The method defined in claim 30 wherein said step of preventing includes the step of sliding a sleeve over said ancillary balloon to prevent a reinflation thereof with fluid.

35. The method defined in claim 30, further comprising the step of tearing off a distal end portion of a sheath enclosing said catheter, said step of tearing being executed prior to said step of inserting, said step of inserting including the step of collapsing said sheath into a folded accordion-like configuration about said catheter at a point of insertion of said catheter into the patient.

36. The method defined in claim 30 wherein said catheter is provided at a proximal end with a hollow catheter plug defining a flash chamber having a transparent wall, further comprising the step of actuating a valve connected to said plug for preventing fluid flow from said chamber.

37. A method for inserting a catheter into a body organ of a patient, comprising the steps of:
providing a catheter enclosed by an internally sterile sheath;
removing a distal end portion of said sheath so as to expose a distal end only of said catheter;
inserting said distal end into a patient; and
manipulating said catheter through said sheath to push said catheter into the patient while simultaneously collapsing said sheath into a shorted accordying-like configuration at a point of insertion of said catheter into the patient;
during said step of inserting and manipulating, engaging said patient about said point of insertion with a flange provided at a distal end of said sheath, said sheath being provided with a score line distally of said flange, said step of removing including the step of tearing off said distal end portion of said sheath at said score line.

38. The method defined in claim 37 wherein said sheath has a body portion containing said catheter and, at a distal end of said body portion, a chamber separable from said body portion, an aliquot of an antibacterial agent being disposed in said chamber, further comprising the steps of (a) tearing off a tip of said sheath to expose said antibacterial agent and (b) applying said antibacterial agent to the patient about said point of insertion prior to said step of removing.

39. The method defined in claim 37 wherein said catheter has an anchor balloon at a distal end, further comprising the steps of:
applying pressure to an ancillary balloon at a proximal end of said catheter to squeeze a pressurizing fluid from said ancillary balloon towards said anchor balloon, upon substantial completion of said steps of inserting and manipulating; and
upon an expansion of said anchor balloon in response to the application of pressure to said ancillary balloon, preventing fluid from flow back from said anchor balloon towards said ancillary balloon.

40. The method defined in claim 37 wherein said catheter is provided at a proximal end with a hollow catheter plug defining a flash chamber having a transparent wall, further comprising the step of actuating a valve connected to said plug for preventing fluid flow from said chamber.

41. A method for inserting a catheter into a body organ of a patient, comprising the steps of:
providing a catheter enclosed by an internally sterile sheath, said sheath having a body portion containing said catheter and further having a chamber separable from said body portion and containing an aliquot of an antibacterial agent;
tearing said sheath to expose said antibacterial agent;

applying said antibacterial agent to a patient about a point of insertion of said catheter into the patient;

acting on said sheath to expose a distal end only of said catheter;

inserting said distal end of said catheter into the patient at said point of insertion upon the application of said antibacterial agent to a patient about said point of insertion; and manipulating said catheter through said sheath to push said catheter into the patient while simultaneously collapsing said sheath into a shortened accordion-like configuration at said point of insertion.

42. The method defined in claim 41 wherein said step of acting includes the step of removing a distal end portion of said sheath to expose the distal end of said catheter.

43. The method defined in claim 42 wherein said chamber is disposed in said distal end portion portion, said step of tearing including the step of separating a distal tip of said sheath along a preformed score line, said step of removing including the step of removing said chamber from said body portion 44. The method defined in claim 43 wherein said step of removing said chamber from said body portion includes the step of separating said chamber from said body portion along an additional preformed score line.

45. The method defined in claim 43 wherein said steps of separating and applying are performed prior to the removal of said distal end portion of said sheath.

* * * * *